United States Patent
Tenn, III (10) Patent No.: US 9,296,768 B2
(45) Date of Patent: Mar. 29, 2016

(54) PROCESS FOR STABILIZING HYDROCYANATION CATALYST

(71) Applicant: INVISTA NORTH AMERICA S.A.R.L., Wilmington, DE (US)

(72) Inventor: William J. Tenn, III, Beaumont, TX (US)

(73) Assignee: INVISTA North America S.a r.l., Wilmington, DE (US)

( * ) Notice: Subject to any disclaimer, the term of this patent is extended or adjusted under 35 U.S.C. 154(b) by 0 days.

(21) Appl. No.: 14/404,037

(22) PCT Filed: May 24, 2013

(86) PCT No.: PCT/US2013/042640
§ 371 (c)(1),
(2) Date: Nov. 26, 2014

(87) PCT Pub. No.: WO2013/181096
PCT Pub. Date: Dec. 5, 2013

(65) Prior Publication Data
US 2015/0148556 A1    May 28, 2015

Related U.S. Application Data

(60) Provisional application No. 61/654,584, filed on Jun. 1, 2012.

(51) Int. Cl.
| | | |
|---|---|---|
| C07F 15/00 | (2006.01) | |
| C07F 9/40 | (2006.01) | |
| C07F 15/04 | (2006.01) | |
| C07F 9/6574 | (2006.01) | |
| C07F 9/145 | (2006.01) | |
| B01J 31/18 | (2006.01) | |
| B01J 31/22 | (2006.01) | |
| C07C 253/10 | (2006.01) | |

(52) U.S. Cl.
CPC ............. *C07F 9/4006* (2013.01); *B01J 31/185* (2013.01); *B01J 31/2221* (2013.01); *C07C 253/10* (2013.01); *C07F 9/145* (2013.01); *C07F 9/65744* (2013.01); *C07F 15/04* (2013.01); *B01J 2231/322* (2013.01); *B01J 2231/70* (2013.01); *B01J 2531/847* (2013.01)

(58) Field of Classification Search
CPC ....... C07F 9/4006; C07F 15/04; C07C 53/10; B01J 31/221
USPC .......................................................... 556/14
See application file for complete search history.

(56) References Cited

U.S. PATENT DOCUMENTS

| | | |
|---|---|---|
| 3,496,215 A | 2/1970 | Drinkard et al. |
| 3,496,217 A | 2/1970 | Drinkard et al. |
| 3,631,191 A | 12/1971 | Kane et al. |
| 3,655,723 A | 4/1972 | Drinkard |
| 3,766,237 A | 10/1973 | Squire et al. |
| 4,874,884 A | 10/1989 | McKinney et al. |
| 5,512,696 A | 4/1996 | Kreutzer et al. |
| 5,688,986 A * | 11/1997 | Tam ................. B01J 31/185 558/337 |
| 5,821,378 A | 10/1998 | Foo et al. |
| 5,959,135 A | 9/1999 | Garner et al. |
| 5,981,772 A | 11/1999 | Foo et al. |
| 6,020,516 A | 2/2000 | Foo et al. |
| 6,127,567 A | 10/2000 | Garner et al. |
| 6,812,352 B2 | 11/2004 | Kreutzer et al. |
| 2004/0122251 A1 | 6/2004 | Rosier et al. |

FOREIGN PATENT DOCUMENTS

| | | |
|---|---|---|
| WO | 2009/091790 A1 | 7/2009 |
| WO | 2012/033556 A1 | 3/2012 |
| WO | 2013/181096 A1 | 12/2013 |

OTHER PUBLICATIONS

Kirpichnikov et al. "Some Unsaturated Esters of Phosphorous Acid", Tr. Kazansk. Khim.—Tekhnol. Inst. No. 30, 1962, pp. 52 to 57 (Russ.).
Liu et al. "2-Alkenylphosphonates and PO-Ylids Derived Thereof in trans Selective Romer-Wittig Olefination Reactions", SYNLETT, vol. 12, 1996, pp. 1197 to 1198.
Tolman et al. "Homogeneous Nickel-Catalyzed Olefin Hydrocyanation", Advances in Catalysis, vol. 33, 1996, pp. 1-46.
International Search Report and Written Opinion received for PCT Patent Application No. PCT/US2013/042640, mailed on Aug. 13, 2013, 13 Pages.
International Preliminary Report on Patentability received for PCT Patent Application No. PCT/US2013/042640, Completed on Apr. 1, 2014, 5 Pages.

* cited by examiner

*Primary Examiner* — Porfirio Nazario Gonzalez
*Assistant Examiner* — Kofi Adzamli
(74) *Attorney, Agent, or Firm* — Robert B. Furr, Jr.

(57) ABSTRACT

The invention provides a method of forming a phosphonate diester compound from a ligand hydrolysis product (LHP) of a phosphite ligand used in a nickel-phosphite hydrocyanation catalyst, such as for conversion of 3-pentenenitrile to adiponitrile, which serves to eliminate acidic LHP compound for a hydrocyanation reaction milieu where the acidic LHP can catalyze further catalyst ligand destruction. The invention further provides phosphonate diester compounds prepared by alkylation of diarylphosphite LHP in the presence of a nickel-phosphite catalyst comprising a bidentate ligand, and a continuous hydrocyanation process for production of adiponitrile wherein catalyst ligand breakdown is inhibited through inactivation of ligand hydrolysis products towards further breakdown. A method of stabilizing a hydrocyanation catalyst is provided.

10 Claims, 5 Drawing Sheets

Figure 1 mixture of isomers

Figure 2

Hydrophosphorylation

PROCESS FOR STABILIZING HYDROCYANATION CATALYST

CROSS-REFERENCE TO RELATED APPLICATION

This application claims benefit of priority from U.S. Provisional Application No. 61/654,584 filed Jun. 1, 2012. This application hereby incorporates by reference this provisional application in its entirety.

FIELD OF THE INVENTION

This disclosure relates to a process for stabilizing nickel-phosphite catalysts used in the manufacture of nitriles from olefins, and in methods using nickel-phosphite catalysts for carrying out the transformation of phosphites to phosphonates.

BACKGROUND OF THE INVENTION

Adiponitrile (ADN) is a commercially important and versatile intermediate in the industrial production of nylon polyamides useful in forming films, fibers, and molded articles. ADN can be produced by hydrocyanation of 1,3-butadiene (BD) in the presence of transition metal complexes including various phosphorus-containing ligands. For example, catalysts including nickel and monodentate phosphorus-containing ligands are well documented in the prior art; see, for example, U.S. Pat. Nos. 3,496,215; 3,631,191; 3,655,723 and 3,766,237; and Tolman, C. A., McKinney, R. J., Seidel, W. C., Druliner, J. D., and Stevens, W. R., Advances in Catalysis, 1985, Vol. 33, pages 1-46. Improvements in the hydrocyanation of ethylenically unsaturated compounds with catalysts including nickel and certain multidentate phosphite ligands are also disclosed; e.g., see: U.S. Pat. Nos. 5,512,696; 5,821,378; 5,959,135; 5,981,772; 6,020,516; 6,127,567; and 6,812,352.

The hydrocyanation of activated olefins such as conjugated olefins (e.g., 1,3-butadiene) can proceed at useful rates without the use of a Lewis acid promoter. However, the hydrocyanation of un-activated olefins, such as 3-pentenenitrile (3PN), require at least one Lewis acid promoter to obtain industrially useful rates and yields for the production of linear nitriles, such as ADN. For example, U.S. Pat. Nos. 3,496,217, 4,874,884, and 5,688,986 disclose the use of Lewis acid promoters for the hydrocyanation of non-conjugated ethylenically unsaturated compounds with nickel catalysts including phosphorus-containing ligands. As a result, in a two-step conversion of BD to ADN, the first hydrocyanation step converting BD to 3PN can be carried out in the absence of a Lewis acid promoter, while the second hydrocyanation step converting 3PN to ADN is facilitated by use of a Lewis acid, e.g., $ZnCl_2$. Typically, such reactions have been run in as complete an absence of water as is practicable, e.g., to avoid phosphite ligand hydrolysis.

As is disclosed in a copending application by Applicants herein, a process for hydrocyanation of 3-pentenenitrile can include feeding 3-pentenenitrile and HCN to a hydrocyanation reaction zone including a Lewis acid promoter, nickel and a phosphorus-containing ligand, in the presence of water, preferably a controlled concentration of water. In that application, incorporated by reference herein in its entirety, the unexpected discovery was disclosed that by maintaining particular concentrations of water in the reaction mixture as the catalyst is recycled through a catalyst recovery process, the hydrocyanation catalyst inventory maintains its activity through a greater number of recycle cycles than other processes that have water at higher or lower, i.e., near zero, concentrations. It is disclosed therein that it was found to be advantageous for various reasons described therein to maintain a range of water concentrations within the reaction zone sufficient to improve activity of the catalyst inventory under continuous operation with downstream liquid-liquid extraction and recycle of the catalyst complex.

However, the presence of water in the hydrocyanation reaction zone, while improving activity of the catalyst inventory, can lead to hydrolysis of certain triarylphosphite ligands of the nickel catalyst to yield acidic phosphite ligand hydrolysis products (LHP), such as diarylphosphites produced by hydrolysis of triarylphosphites, that can undergo further degradation to monoarylphosphites and phosphorous acid. Insomuch as the ligand hydrolysis process itself can be acid-catalyzed, the buildup of acidic LHP can further increase the rate of ligand hydrolysis, degrading the active nickel-phosphite hydrocyanation catalyst.

SUMMARY OF THE INVENTION

The inventors herein have unexpectedly discovered that the buildup of acidic ligand hydrolysis products (LHP), and the resulting accelerated breakdown of a nickel-phosphite catalyst used in hydrocyanation reactions, e.g., hydrocyanation of butadiene, or hydrocyanation of pentenenitrile, such as in the presence of a Lewis acid, hydrogen cyanide, and water, can be reduced or eliminated by adding a bidentate phosphite ligand as disclosed herein to the hydrocyanation milieu including a nickel-phosphite catalyst, or by using a nickel-phosphite catalyst comprising a bidentate ligand as disclosed herein. The present application relates to methods of converting acidic LHP diarylphosphites to neutral phosphonate diester products that do not catalyze the degradation of the phosphite ligands of the nickel-phosphite catalyst. The invention also relates to the neutral phosphonate products of such conversions. The invention also relates to pentenenitrile hydrocyanation reactions wherein ligand degradation is inhibited and catalyst life is prolonged; and the invention also relates to methods of stabilizing nickel-phosphite catalysts for pentenenitrile hydrocyanation under conditions where water is present.

DETAILED DESCRIPTION OF THE INVENTION

Reference in the specification to an "example," "embodiment," etc., indicates that the described example of embodiment can include a particular feature, structure, or characteristic, but every example or embodiment may not necessarily include the particular feature, structure, or characteristic. Moreover, such phrases are not necessarily referring to the same example or embodiment. Further, when a particular feature, structure, or characteristic is described in connection with an example or embodiment, it is submitted that it is within the knowledge of one skilled in the art to affect such feature, structure, or characteristic in connection with other examples or embodiments whether or not explicitly stated.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a concentration range of "about 0.1% to about 5%" should be interpreted to include not only the explicitly recited concentration of about 0.1 wt % to about 5 wt %, but also the individual concentrations (e.g., 1%, 2%, 3%, and 4%) and the sub-ranges (e.g., 0.5%, 1.1%, 2.2%, 3.3%, and 4.4%) within the indicated range.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their features are intended to include only "chemically feasible" structures, and any recited structures that are not chemically feasible, for example in a structure shown with variable atoms or groups, are not intended to be disclosed or claimed herein.

All chiral, diastereomeric, racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

When a group, e.g., an "alkyl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, less than the total number of carbon atoms in the universe and bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded, as the number of atoms in the group cannot be infinite.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

The compound or set of compounds, such as are used in the inventive methods, can include any one of any of the combinations and/or sub-combinations of the features listed herein.

A compound as shown in any of the Examples, or among the exemplary compounds, is also provided.

Provisos may apply to any of the disclosed categories or groups, wherein any one or more of the other disclosed categories, groups, features, compounds or species may be excluded from such categories or groups.

An "aryl" group, as the term is used herein, refers to cyclic aromatic hydrocarbons that do not contain heteroatoms in the ring. Thus aryl groups include, but are not limited to, phenyl, naphthyl, azulenyl, heptalenyl, biphenyl, binaphthyl, indacenyl, fluorenyl, phenanthrenyl, triphenylenyl, pyrenyl, naphthacenyl, chrysenyl, biphenylenyl, and anthracenyl, which can be unsubstituted, or which can be substituted, e.g., with alkyl groups. Aryl groups can contain about 6 to about 14 carbons in the ring portions of the groups. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above. A "biaryl" group, as the term is used herein, refers to subgenus of an aryl group wherein two ring systems are connected by a linker, which can be a bond, an atom such as oxygen, a linker such as a methylene, or the like, such that two aromatic rings are covalently connected. Examples are biphenyl and binaphthyl.

An alkyl group, as the term is used herein, refers to straight chain and branched alkyl groups having from 1 to about 20 carbon atoms, and typically from 1 to 12 carbons or from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl.

The terms "monodentate" and "bidentate", as the terms are used herein with respect to phosphite ligands, refers to molecular entities comprising one or two metal-complexing phosphorus atoms, respectively. The phosphites, both monodentate and bidentate, form complexes with nickel atoms that, such as in the presence of Lewis acids and water, can catalyze hydrocyanation reactions, e.g., of pentenenitriles to adiponitrile.

Examples of monodentate phosphite ligands, as the term is used herein, include triarylphosphite structures such as compounds of the formula wherein each Ar represents an aryl group, which can be the same or different. For example, all three Ar groups can be 2,4-xylyl groups, providing a monodentate ligand of formula

(Ligand 1)

suitable for complexation of metals such as nickel in various oxidation states. In this type of molecular entity, each phosphorus atom is bonded to three substituted phenyl rings, each via a respective oxygen atom, i.e., by three monofunctional aryl groups.

Additional examples of monodentate phosphite ligands, as the term is used herein, include cyclic phosphites containing a single phosphorus atom, such as compounds of the formula

(Ligand 2)

In molecular entities of this type, each phosphorus atom is bonded to a substituted phenyl via an oxygen atom, and twice to a substituted biphenyl via two respective oxygen atoms, i.e., the phosphite is esterified by one monofunctional aryl group and one bifunctional aryl group.

A bidentate phosphite ligand, as the term is used herein, refers to molecular entities comprising two phosphorus atoms per molecule. Both phosphorus atoms are bonded to a bifunctional aryl group, and can be bonded to additional monofunctional or bifunctional aryl groups. An example is (Ligand 3)

Another example is (Ligand 4)

wherein each of the two phosphorus atoms is bonded to a bifunctional aryl group, e.g., a biphenyl or binaphthyl, each phosphorus atom being bonded through a respective oxygen atom, and each of the two phosphorus atoms being further bonded to two respective monofunctional aryl groups.

A phosphite or phosphite ester, as the term is used herein, refers to a compound comprising one or more trivalent phosphorus atoms, each phosphorus atom being bonded to three oxygen atoms, each of which oxygen atoms can bear a proton, or can be bonded to a carbon moiety. A triarylphosphite ester, termed a "triarylphosphite", is a compound where each of the three oxygen atoms bears an aryl group, and is of formula (ArO)$_3$P, wherein each independently selected Ar represents an aryl group. An example of a triarylphosphite is Ligand 5, a mixture of isomers of the general formula wherein R is methyl.

A "diarylphosphite" is a compound of formula (ArO)$_2$POH, again, wherein each independently selected Ar represents an aryl group. As can be seen a diarylphosphite contains an OH group or its equivalent, which comprises an acidic proton, conferring the nature of an acid on a diarylphosphite. The term embodies both tautomeric forms, often depicted as shown below:

Regardless of the position of bonding of the hydrogen atom, such compounds possess acidic properties.

A "monoarylphosphite" is a compound of formula (ArO)P(OH)$_2$. The presence of the free OH groups or equivalents thereof also confers acidic properties on monoarylphosphites. The free acid is phosphorous acid, H$_3$PO$_3$, as is well known in the art.

A "phosphonate ester" as the term is used herein, an ester of a phosphonic acid, comprises a phosphorus-carbon bond, a pentavalent phosphorus atom, and three oxygen atoms bonded to the phosphorus atom, two of which are available to form a further bond with a proton or with a carbon moiety.

If both available oxygen atoms are bonded to a carbon moiety, the resulting compound is a phosphonate diester, e.g. a diaryl phosphonate diester R—P(=O)(OAr)$_2$; if only one, a phosphonate monoester, e.g., a monoaryl phosphonate ester R—P(=O)(OAr)(OH). The free acid is a phosphonic acid, R—P(=O)(OH)$_2$. While phosphonate monoesters and free acids have acidic properties, phosphonate diesters have no ionizable proton, thus are non-acidic, termed "neutral" phosphonate esters or phosphonate diesters.

The formation of the neutral phosphonate diester products from the acidic diarylphosphite ligand hydrolysis products by a method of the invention involves the direct alkylation of the phosphorus atom of the diarylphosphite LHP with reagents present in the hydrocyanation reaction mixture, such as pentenenitriles, butadiene, butadiene dimers and their hydrocyanation products, and the like, yielding phosphonates and the like. Analogously, if further ligand hydrolysis of a diarylphosphite took place in the reaction milieu of the hydrocyanation process, the inventor recognizes that such monoarylphosphites would be also be converted similarly to neutral species in which the acidic OH group has been neutralized by an alkylation process. Thus, the formation of acidic LHP products capable of catalyzing catalyst ligand hydrolysis is diminished by use of a method of the invention.

A "Lewis acid" is a compound that can act as an electron acceptor, as is well known in the art. Various metal halides, such as ZnCl$_2$, are examples of Lewis acids.

One aspect of the invention is a method of forming a phosphonate diester compound of formula (I)

wherein each Ar is independently an unsubstituted or a mono-substituted or a multi-substituted aryl group, wherein any aryl group can be substituted with independently selected (C1-C4)alkyl, hydroxyl, a phosphite ester group, or phosphonate ester group; or, the two Ar groups are bonded to each other to provide an unsubstituted or substituted biaryl derivative, wherein the biaryl derivative is unsubstituted or is independently mono-substituted or multi-substituted with independently selected (C1-C4)alkyl, hydroxyl, a phosphite ester group, or a phosphonate ester group; and, R is a 2-butenyl, 3-butenyl, 2-cyanobutyl, 3-cyanobutyl, or 4-cyanobutyl group;

the method comprising contacting in a reaction zone a diaryl phosphite compound of formula (III), wherein Ar is as defined for the compound of formula (I), a pentenenitrile, hydrogen cyanide, a Lewis acid, and water, in the presence of a nickel catalyst comprising a bidentate phosphite ligand of formula (IV)

(IV)

wherein $R^1$ and $R^2$ are each independently an unsubstituted or a substituted monovalent aryl, and each of $R^3$-$R^{10}$ is independently selected from the group consisting of hydrogen, (C1-C10) alkyl, and (C1-C10)alkoxy, or wherein two adjacent $R^3$ groups together form an optionally substituted fused aryl ring, under conditions suitable for hydrocyanation of the pentenenitrile to occur.

For the bidentate phosphite ligand of formula (IV), $R^1$ and $R^2$ can both be mono-ortho-substituted aryls, wherein the $R^1$ and $R^2$ aryl groups are each ortho-substituted with one respective (C1-C10)alkyl or (C1-C10)alkoxy group, provided that respective meta- and para-positions of the $R^1$ and $R^2$ aryls can be unsubstituted or substituted.

For the bidentate phosphite ligand of formula (IV), $R^6$ and $R^{10}$ are preferably not hydrogen.

For the bidentate phosphite ligand of formula (IV), at least one of $R^3$-$R^5$, and at least one of $R^7$-$R^9$, is preferably not hydrogen.

For the bidentate phosphite ligand of formula (IV), $R^5$ and $R^6$ together can optionally form a (C1-C10)alkyl or a (C1-C10)alkoxy substituted fused phenyl ring, and wherein $R^9$ and $R^{10}$ together form an optionally (C1-C10)alkyl or a (C1-C10)alkoxy substituted fused phenyl ring.

For the bidentate phosphite ligand of formula (IV), $R^1$ and $R^2$ can both be mono-ortho-substituted aryls and the aryls are ortho-substituted with one respective (C1-C10)alkyl or a (C1-C10)alkoxy, provided that respective meta- and para-positions of the $R^1$ and $R^2$ aryls can be unsubstituted or substituted; $R^6$ and $R^{10}$ are a (C1-C10)alkyl or a (C1-C10)alkoxy, and at least one of $R^3$-$R^5$, and at least one of $R^7$-$R^9$, is a (C1-C10)alkyl or a (C1-C10)alkoxy.

More specifically, the pentenenitrile can be 3-pentenenitrile.

$R^1$ and $R^2$ of formula (IV) can also be 2,4-xylyl.

$R^3$ and $R^7$ can also be isopropyl, $R^4$ and $R^8$ can be hydrogen, or $R^5$, $R^6$, $R^9$ and $R^{10}$ can be methyl, or any combination thereof.

More specifically, the bidentate phosphite ligand of formula (IV) can be

(Ligand 3)

or can be

(Ligand 4)

In a catalytic complex with nickel, in the presence of a Lewis acid, $ZnCl_2$, an active catalytic form in which these bidentate phosphate ligands are present in a hydrocyanation reaction zone, is believed to be of the following structures:

, and

-continued respectively.

The invention also relates to a phosphonate diester compound of formula (I)

wherein
each Ar is independently an unsubstituted or a mono-substituted or a multi-substituted aryl group, wherein any aryl group can be substituted with independently selected (C1-C4)alkyl, hydroxyl, a phosphite ester group, or phosphonate ester group; or, the two Ar groups are bonded to each other to provide an unsubstituted or substituted biaryl group, wherein the biaryl group is unsubstituted or is independently mono-substituted or multi-substituted with independently selected (C1-C4) alkyl, hydroxyl, a phosphite ester group, or a phosphonate ester group; and, R is a 2-butenyl, 3-butenyl, 2-cyanobutyl, 3-cyanobutyl, 4-cyanobutyl group, or is one of a group of isomers of a cyanononenyl group wherein the group of isomers includes double bond and cyano group positional isomers.

R can be 2-butenyl or 3-butenyl. R can also be 2-cyanobutyl, 3-cyanobutyl, or 4-cyanobutyl, or R can be one of a group of isomers of a cyanooctenyl group wherein the group of isomers includes double bond and cyano group positional isomers. A cyanooctenyl group as the term is used herein refers to a group comprising eight carbon atoms, a cyano group including a carbon atom, and a double bond in any of the possible isomeric configuration, to provide a group with a total of nine carbon atoms, a nitrile functionality, and an unsaturation. For example, a cyanooctenyl group can include a group of formula wherein a wavy line indicates a bond by which the cyanooctenyl group is bonded to the phosphorus atom of the phosphonate, i.e., an 8-cyano-oct-3-enyl group.

For the phosphonate diester compound of formula (I), both Ar groups can be (C1-C4)alkyl substituted phenyl, or both Ar groups taken together can be (C1-C4)alkyl multisubstituted biphenyl, or one Ar group can be (C1-C4)alkyl substituted phenyl and one Ar group can be a (C1-C4)alkyl multisubstituted biphenyl further substituted with a hydroxyl.

The compound of formula (I) can be selected from the group consisting of wherein R is defined above, i.e., 2-butenyl, 3-butenyl, 2-cyanobutyl, 3-cyanobutyl, 4-cyanobutyl, or a cyanooctenyl isomer.

The invention also relates to a continuous hydrocyanation process for production of adiponitrile, comprising use of a nickel-phosphite catalyst composed of nickel and a ligand mixture comprising one or more monodentate phosphite ligand and the bidentate phosphite ligand of formula (IVA)

(IVA)

wherein $R^1$ and $R^2$ are both mono-ortho-substituted aryls and the aryls are ortho-substituted with one respective (C1-C10) alkyl or (C1-C10)alkoxy, provided that respective meta- and para-positions of the $R^1$ and $R^2$ aryls can be unsubstituted or substituted; $R^6$ and $R^{10}$ are a (C1-C10)alkyl or a (C1-C10) alkoxy, $R^3$-$R^5$ and $R^7$-$R^9$ are each independently hydrogen, a (C1-C10)alkyl or a (C1-C10)alkoxy, provided that at least one of $R^3$-$R^5$, and at least one of $R^7$-$R^9$, is a (C1-C10)alkyl or a (C1-C10)alkoxy; wherein the process exhibits reduced degradation of the catalyst relative to an amount of degradation of a second nickel-phosphite catalyst under comparable conditions wherein the ligand mixture comprises only one or more monodentate phosphite ligands, or, comprising bidentate ligands not including a compound of formula (IVA), the process comprising:

(a) charging the catalyst, 3-pentenenitrile, a Lewis acid, HCN, and water, to a reaction zone under conditions suitable for hydrocyanation to occur;

(b) withdrawing reactor effluent comprising a hydrocyanation product and recovered catalyst from the reaction zone;

(c) contacting the reactor effluent with an extraction solvent to separate recovered catalyst from hydrocyanation product; and (d) recharging a portion of the recovered catalyst and a portion of makeup catalyst to the reaction zone, sufficient to maintain substantially constant over a period of time of a ratio of an amount of active catalyst to an amount of an amount of 3-pentenenitrile added over the period of time, wherein a relative portion of makeup catalyst is reduced compared to a relative portion of makeup catalyst used in carrying out a comparable process wherein the ligand mixture comprises only monodentate phosphite ligands or comprises a bidentate ligand not including the compound of formula (IVA).

In the above-described process, a portion of makeup catalyst recharged to the reaction zone of the catalyst comprising the bidentate phosphite ligand of formula (IVA) can be less than a portion of makeup catalyst charged to the reaction zone of the catalyst comprising only one or more monodentate phosphite ligands or comprising a bidentate ligand not including the compound of formula (IVA).

More specifically, the bidentate phosphite ligand of formula (IVA) can be Ligand 3

Ligand 3 or can be Ligand 4

Ligand 4 or a mixture thereof, and wherein reduced degradation of the catalyst occurs compared to the degradation of the catalyst that occurs in carrying out a comparable process wherein the ligand mixture does not include Ligand 3 or Ligand 4.

The disclosed hydrocyanation process of the invention can include controlling the amount of water in the reaction zone. The process is suitably operated continuously to recycle the catalyst complex. Thus, for example, the process can include hydrocyanating 3-pentenenitrile in a reaction zone in the presence of a catalyst complex comprising a phosphorus-containing ligand and nickel metal, comprising flowing 3-pentenenitrile, Lewis acid, HCN and a controlled amount of water to the reaction zone; withdrawing reactor effluent comprising hydrocyanation product and catalyst complex from the reaction zone; contacting the reactor effluent with extraction solvent to recover catalyst complex and remove impurities from the catalyst complex; and recycling at least a portion of the recovered catalyst complex to the reaction zone. The process can include controlling the water concentration in the reaction zone to maintain a desired catalyst composition in the circulating catalyst inventory. The inventor herein has unexpectedly discovered that the use of a bidentate phosphite ligand of formula (IV) or of formula (IVA) as disclosed herein reduces the rate of catalyst decomposition during execution of the hydrocyanation process, compared to a comparable process wherein no bidentate ligands of formula (IV) or of formula (IVA) as disclosed herein are employed. This provides for a reduction in the amount of makeup catalyst that would be needed to maintain a substantially constant ratio of an amount of active catalyst to an amount of an amount of 3-pentenenitrile in the reaction zone.

Examples of suitable water concentrations include 0.5 ppm up to the saturation limit of the reaction mixture, for example 0.5 ppm to about and about 2000 ppm, or about 1 ppm and 1000 ppm, or from about 5 ppm to about 500 ppm, or from about 10 ppm to about 350 ppm, or from about 20 ppm to about 300 ppm, or at about 240 ppm.

The use of controlled water concentrations in the hydrocyanation reaction, contrary to the understanding of the person of ordinary skill is surprising, because it has been generally understood that water causes degradation of the catalyst complex, thus it is generally taught that the concentration of water should be kept as low as possible in the reaction mixture to maximize the activity of the catalyst complex through repeated recycling cycles. This subject matter is disclosed in copending patent application by the inventors herein.

It has been unexpectedly discovered by the inventor herein that use of a bidentate ligand of formula (IV), or of formula (IVA), as disclosed herein, in a hydrocyanation process wherein water is present as can be carried out to obtain the benefits described in the above-referenced copending patent application, can suppress the buildup or concentration increase in the reaction milieu of acidic ligand hydrolysis products (LHP) that can themselves catalyze further ligand hydrolysis. This is accomplished through the catalytic conversion of the acidic ligand hydrolysis products to neutral phosphonate diester compounds in the presence of the nickel-phosphite catalyst wherein a bidentate ligand, e.g., of formula (IV), or of formula (IVA), as disclosed herein, is present. The present invention can provide a more efficient process of hydrocyanating 3-pentenenitrile in the production of adiponitrile than other processes, for example, by making more efficient use of the valuable ligand or catalyst derived from the ligand, including by maintaining the catalytic activity of the ligand or catalyst formed from the ligand at a higher level though successive recycling of the ligand-containing catalyst complex.

The invention also relates to a continuous hydrocyanation process for production of adiponitrile as described above wherein bidentate phosphite ligand of formula (IV) or of formula (IVA) is Ligand 3 or Ligand 4, or a mixture thereof, and wherein reduced degradation of the catalyst occurs compared to the degradation of the catalyst that occurs in carrying out a comparable process wherein the ligand mixture does not include Ligand 3 or Ligand 4.

The invention also relates to a method of converting an acidic phosphite ligand hydrolysis product of formula (III)

wherein each Ar is independently an unsubstituted or a mono-substituted or a multi-substituted aryl group, wherein any aryl group can be substituted with independently selected (C1-C4)alkyl, hydroxyl, a phosphite ester group, or phosphonate ester group; or, the two Ar groups are bonded to each other to provide an unsubstituted or substituted biaryl group, wherein the biaryl group is unsubstituted or is independently mono-substituted or multi-substituted with independently selected (C1-C4) alkyl, hydroxyl, a phosphite ester group, or a phosphonate ester group;

to an electrically neutral phosphonate ester form;

the method comprising contacting the ligand hydrolysis product of formula (III) and an unsubstituted or substituted alkene in the presence of a bidentate phosphite ligand of formula (IV)

wherein $R^1$ and $R^2$ are each independently an unsubstituted or a substituted monovalent aryl, and each of $R^3$-$R^{10}$ is independently selected from the group consisting of hydrogen, (C1-C10) alkyl, and (C1-C10)alkoxy, or wherein two adjacent $R^3$-$R^{10}$ groups together form an optionally substituted fused aryl ring;

in the presence of the alkene, hydrogen cyanide, and water, in a hydrocyanation reaction zone, under conditions suitable to produce the electrically neutral phosphonate ester form thereof.

For the bidentate phosphite ligand of formula (IV), $R^1$ and $R^2$ can both be mono-ortho-substituted aryls, wherein the aryl groups $R^1$ and $R^2$ are respectively mono-ortho-substituted with a (C1-C10)alkyl or a (C1-C10)alkoxy group. The aryl groups can be meta- and/or para-substituted, but in these cases, each of $R^1$ and $R^2$ may bear only a single alkyl or alkoxy substituent, as defined.

For the bidentate phosphite ligand of formula (IV), $R^6$ and $R^{10}$ are preferably not hydrogen.

For the bidentate phosphite ligand of formula (IV), at least one of $R^3$-$R^5$, and at least one of $R^7$-$R^9$, is preferably not hydrogen.

For the bidentate phosphite ligand of formula (IV), $R^5$ and $R^6$ together can optionally form a (C1-C10)alkyl or a (C1-C10)alkoxy substituted fused phenyl ring, and wherein $R^9$ and $R^{10}$ together form an optionally (C1-C10)alkyl or a (C1-C10)alkoxy substituted fused phenyl ring.

For the bidentate phosphite ligand of formula (IV), $R^1$ and $R^2$ can both be mono-ortho-substituted aryls and the aryls are ortho-substituted with a (C1-C10)alkyl or a (C1-C10)alkoxy, $R^6$ and $R^{10}$ are a (C1-C10)alkyl or a (C1-C10)alkoxy, and at least one of $R^3$-$R^5$, and at least one of $R^7$-$R^9$, is a (C1-C10)alkyl or a (C1-C10)alkoxy.

For example, $R^1$ and $R^2$ can be 2,4-xylyl.

For example, the compound of formula (IV) can be (Ligand 3)

or is (Ligand 4)

More specifically, in the process, the alkene can be a pentenenitrile, such as 3-pentenenitrile.

The invention also relates to a method of stabilizing a hydrocyanation catalyst with respect to hydrolytic ligand decomposition under reaction conditions effective for hydrocyanation of a pentenenitrile in the presence of a Lewis acid and water, the catalyst comprising a nickel-phosphite complex composed of nickel and one or more triarylphosphite ligand, the method comprising addition of a bidentate phosphite ligand to the nickel-phosphite complex, the bidentate ligand being of formula (IV)

(IV)

wherein $R^1$ and $R^2$ are each independently an unsubstituted or substituted monovalent aryl group; each of $R^3$-$R^{10}$ is independently selected from the group consisting of hydrogen and $C_{1-10}$ alkyl, or wherein two adjacent $R^3$-$R^{10}$ groups together form an optionally substituted fused aryl ring.

For example, for the bidentate phosphite ligand of formula (IV), $R^1$ and $R^2$ can both be mono-ortho-substituted aryls, wherein the aryl groups are ortho-substituted with a (C1-C10) alkyl or a (C1-C10)alkoxy group. For example, $R^1$ and $R^2$ can be 2,4-xylyl. Or, for the bidentate phosphite ligand of formula (IV), $R^6$ and $R^{10}$ may not hydrogen.

For the bidentate phosphite ligand of formula (IV), at least one of $R^3$-$R^5$, and at least one of $R^7$-$R^9$, is preferably not hydrogen. Or, for the bidentate phosphite ligand of formula (IV), $R^5$ and $R^6$ together can optionally form a (C1-C10)alkyl or a (C1-C10)alkoxy substituted fused phenyl ring, and wherein $R^9$ and $R^{10}$ together can optionally form an (C1-C10) alkyl or a (C1-C10)alkoxy substituted fused phenyl ring.

More specifically, for the bidentate phosphite ligand of formula (IV), $R^1$ and $R^2$ can both be mono-ortho-substituted aryls and the aryls can be ortho-substituted with a (C1-C10) alkyl or a (C1-C10)alkoxy, $R^6$ and $R^{10}$ can be a (C1-C10)alkyl or a (C1-C10)alkoxy, and at least one of $R^3$-$R^5$, and at least one of $R^7$-$R^9$, can be a (C1-C10)alkyl or a (C1-C10)alkoxy.

More specifically, in the inventive process, the pentenenitrile is 3-pentenenitrile.

More specifically, the bidentate phosphite ligand of formula (IV) can be (Ligand 3)

or can be (Ligand 4)

Figure 1:
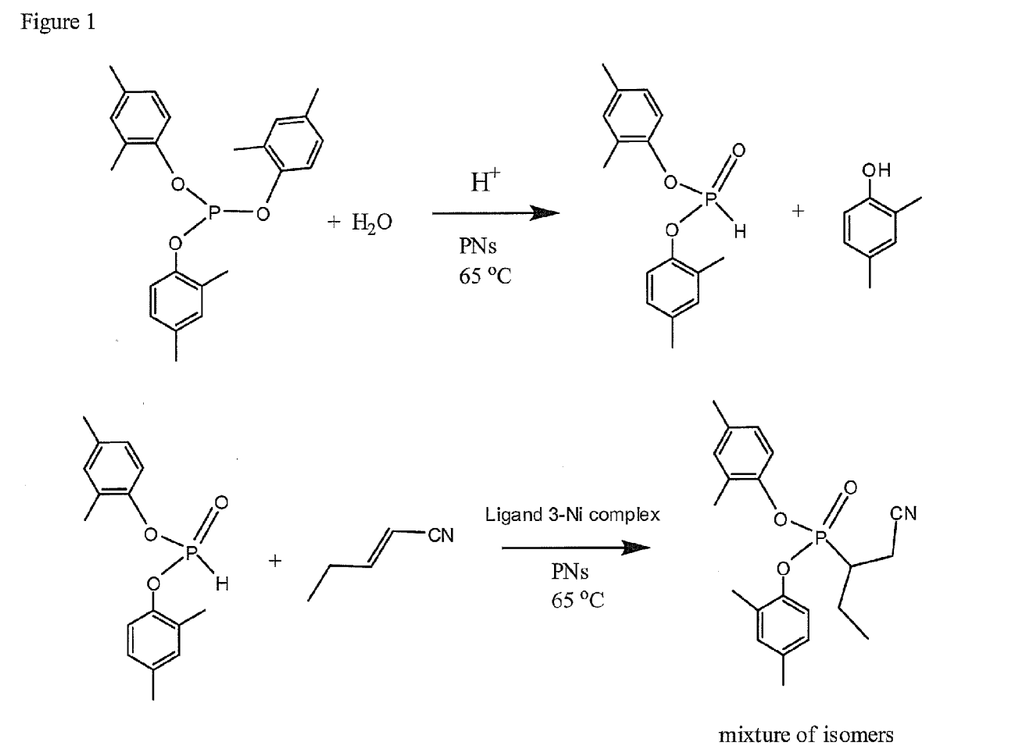
FIG. 1 shows a scheme illustrating what is believed to be the reactions for formation and inactivation of Ligand Hydrolysis Products (LHP); the upper reaction illustrates formation of LHP, and the lower reaction the alkylation inactivation of acidic LHPs.

FIG. 1 illustrates reactions that occur in carrying out a process of the invention. A catalyst comprising a nickel complex with a ligand such at tris-(2,4-xylyl)phosphite, the compound shown undergoing reaction with water in the presence of acid (H$^+$) and pentenenitriles ("PNs"), yields the free 2,4-xylenol and the diarylphosphite LHP as shown.

In the second step of FIG. 1, the diaryl phosphite illustratively undergoes reaction with 2-pentenenitrile in the presence of a catalyst comprising a bidentate ligand (Ligand 3)-nickel complex, yielding a phosphonate diester of the invention, which is non-acidic and does not catalyze further ligand hydrolysis in the presence of water. The 2-pentenenitrile, 3-pentenenitrile, and 4-pentenenitrile isomeric compounds are believed to be interchangeable under the conditions of the hydrocyanation reaction.

Figure 2:
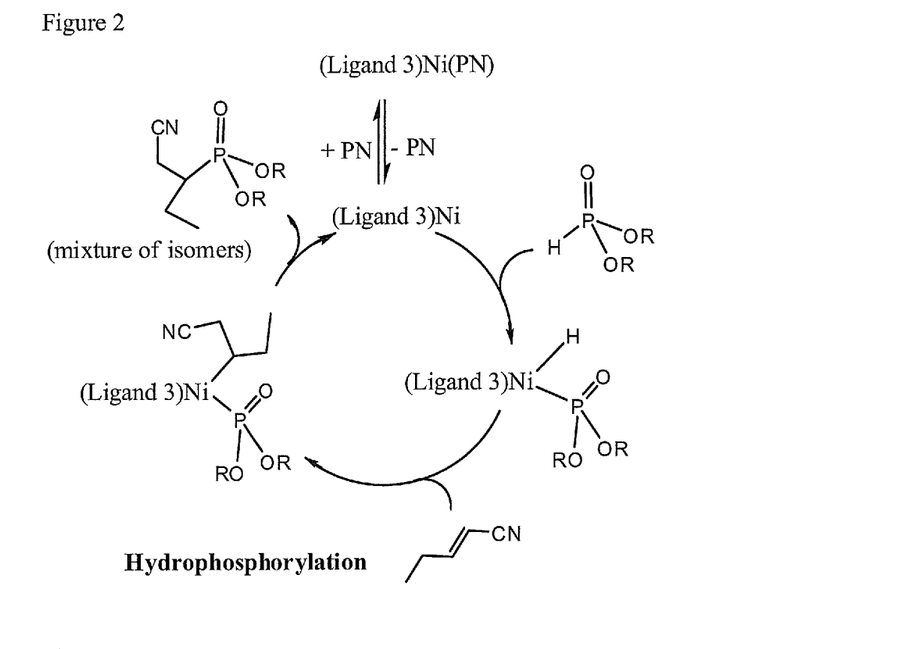
FIG. 2 shows a reaction scheme illustrating what is believed to be a mechanism for formation of a cyanobutylphosphonate from a diarylphosphite LHP.

Although not wishing to be bound by theory, FIG. 2, illustrates what the inventor herein believes to be a cycle of reactions by which the LHP inactivation and formation of cyanobutylphosphonate diesters is achieved. The diarylphosphite LHP (i.e., wherein R=aryl) is believed to complex with the nickel-phosphite catalyst comprising the bidentate ligand (here, for example, Ligand 3), then to react with a pentenenitrile (for example, 2-pentenenitrile) to produce an isomeric mix of cyanobutylphosphonates.

Figure 3:
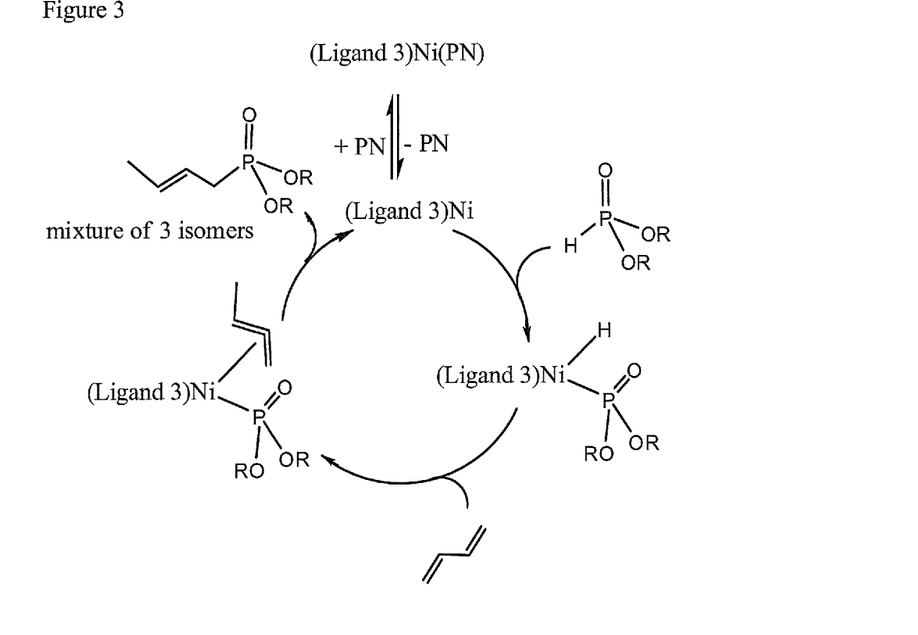
FIG. 3 shows a reaction scheme illustrating what is believed to be a mechanism for formation of a butenylphosphonate from a diarylphosphite LHP.

FIG. 3 illustrates what the inventor believes to be a cycle of reactions by which the LHP inactivation and formation of butenylphosphonate diesters is achieved, by an analogous mechanism except reacting with butadiene, which can be present in the reaction milieu of hydrocyanation of pentenenitriles, through reverse reaction, elimination of HCN.

Figure 4:
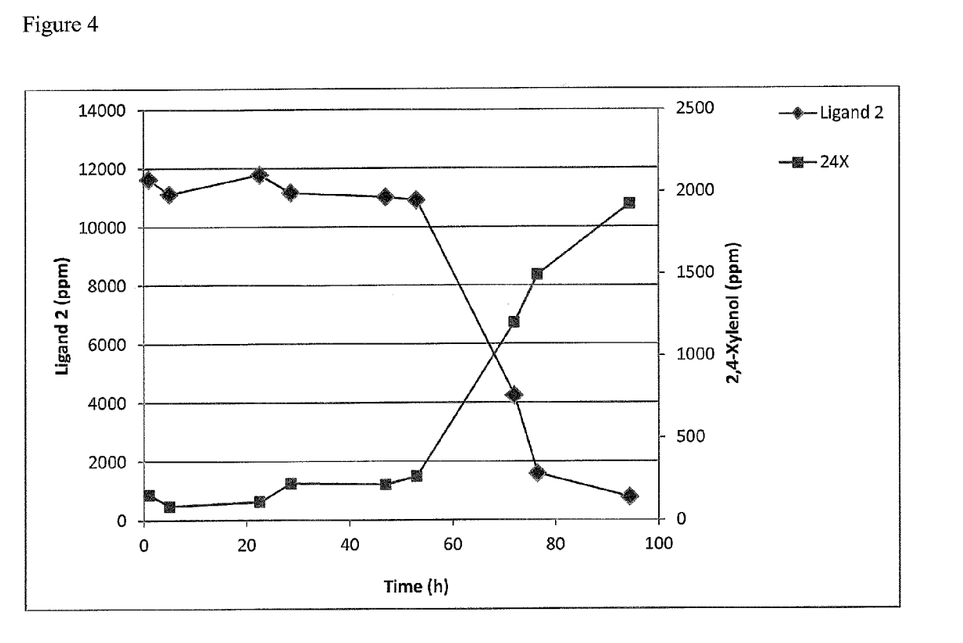
FIG. 4 is a graph showing a time course of LHP formation over time resulting from the hydrolysis of Ligand 2 in pentenenitrile in the presence of water and, at 48 hours, $ZnCl_2$.

FIG. 4 shows a time course of LHP formation over time for ligand Ligand 2. The study was carried out using Ligand 2 in cis-2PN containing 2500 ppm water, maintained at 75° C. for 2 days and then 500 ppm ZnCl$_2$ added. As can be seen, significant ligand (Ligand 2) hydrolysis and formation of 2,4-xylenol, the byproduct of LHP formation, occurs when the Lewis acid ZnCl2 is added to the reaction milieu.

Figure 5:
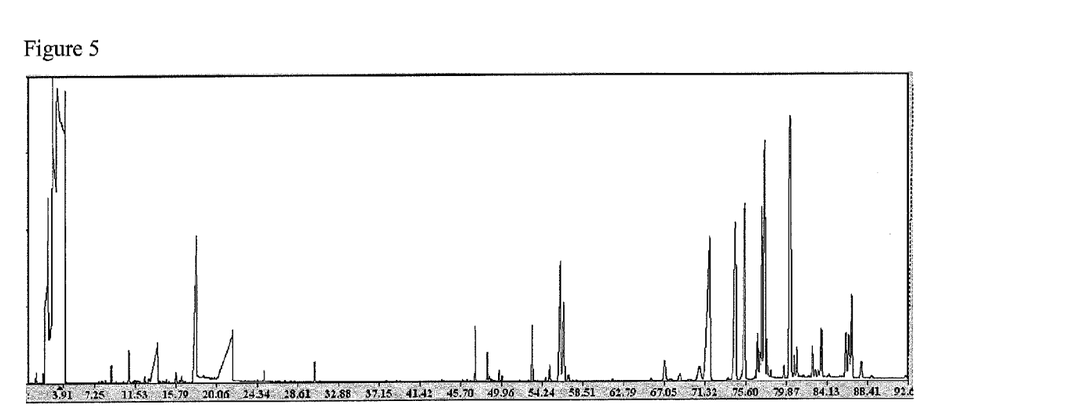
FIG. 5 shows a GC/MS trace of catalyst ligand byproducts after standing at 75° C., in the presence of 500 ppm $H_2O$, for 5 days, in the presence of bidentate Ligand 3.

FIG. 5 shows a gas chromatography/mass spectrometry trace of a nickel-phosphite catalyst comprising a bidentate phosphite ligand Ligand 3, after 5 days at 75° C., in the presence of 500 ppm H$_2$O. Consistent with $^{31}$P NMR results, butenyl and cyanobutyl phosphonates are observed in significant quantities in hydrolyzed catalyst samples, but no acidic diarylphosphite LHPs are present. In the absence of the bidentate ligand, acidic LHP products are observed.

EXAMPLES

Example 1

Figure 6:
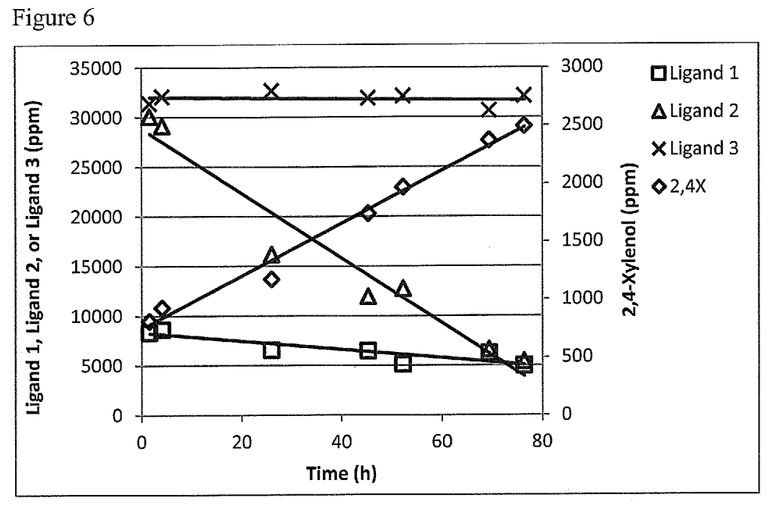
FIG. 6 is a graph showing the rate of hydrolysis of a mixture of Ligand 1, Ligand 2, and Ligand 3, in the presence of the Ligand 3-nickel complex. See Example 1.

Hydrolysis of a Mixture of Ligand 1, Ligand 2, and Ligand 3, Wherein the Nickel Phosphite Complex Formed from Ligand 3 is Present in the Mixture The experiment was conducted in a 10 mL, thick-walled, conical Reacti-Vial™ using a temperature-regulated Reacti-Block™ aluminum heating block. Mixing was accomplished using a triangular magnetic stir bar. The heating block was enclosed in a nitrogen purge box. The Reacti-vial™ is charged with a solution of the Formula Ligand 3-Nickel complex in pentenenitriles in which Ligand 1 and Ligand 2 are also present, inside a glove-box and then with water by microsyringe once transferred to the heating block at the beginning of the experiment. The initial water concentration was 2500 ppm and the Reacti-Block™ was maintained at 75° C. Samples were then removed at the desired intervals for analysis by HPLC. At the conclusion of the studies, $^{31}$P NMR was also obtained on selected samples. See FIG. 6 and Table 1 for analytical results data. Ligand 1 and Ligand 2 are monodentate phosphite ligands, Ligand 3 is a bidentate phosphite ligand, and 2,4X is 2,4-xylenol.

Comparative Example A

Figure 7:
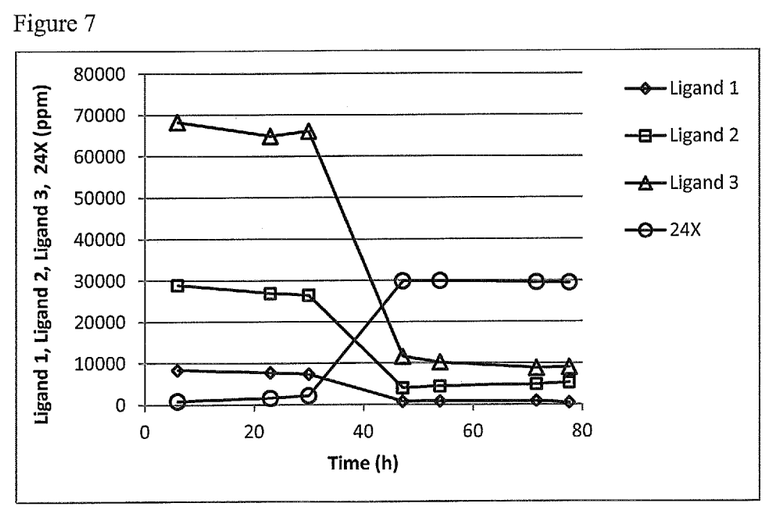
FIG. 7 is a graph showing the results of the control experiment for Example 1, wherein in the absence of nickel, hydrolysis of Ligand 1, Ligand 2 and Ligand 3 and formation of LHP and byproduct 2,4X exhibit an induction period followed by an accelerated phosphite hydrolysis rate, characteristic of an auto-catalytic reaction.

Hydrolysis of a Mixture of Ligand 1, Ligand 2, and Ligand 3 without the Nickel Catalyst Present The experiment Example 1 was replicated but, eliminating the addition of the nickel metal, the hydrolysis of Ligand 1, Ligand 2, and Ligand 3 and the buildup of 2,4X over time occurs. The data show that the hydrolysis of the phosphites exhibits an induction period followed by acceleration in rate, which is characteristic of an auto-catalytic reaction. See FIG. 7 and Table 1 for analytical results data.

Comparative Example B

Figure 8:
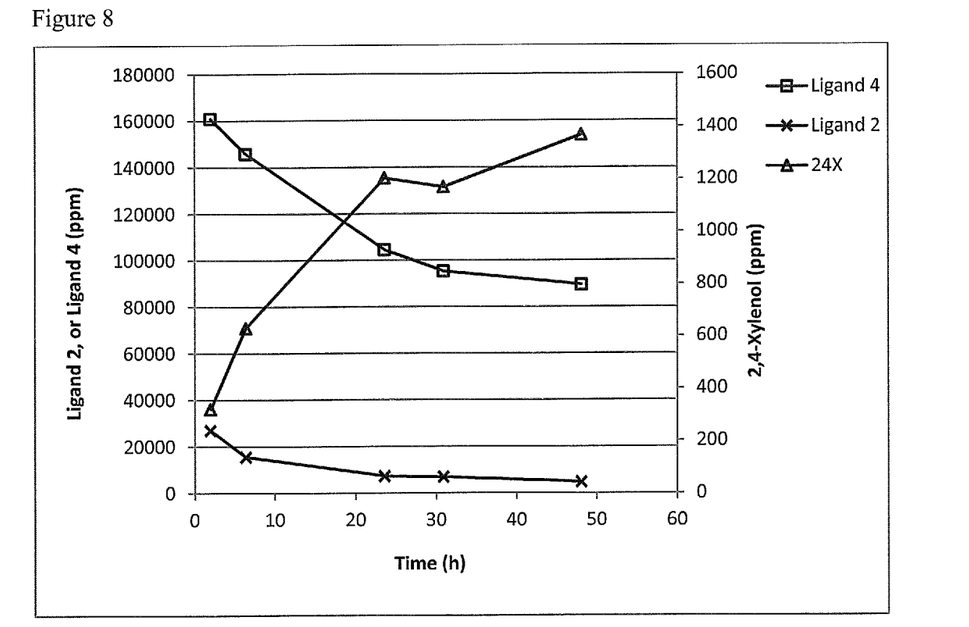
FIG. 8 shows a graph of the time course of hydrolysis of a mixture of Ligand 2, and Ligand 4, in the presence of the Ligand 4-nickel complex.

Hydrolysis of Ligand 2, Wherein the Nickel Phosphite Complex Formed from Ligand 4 is Present in the Mixture Example 1 was replicated, but replacing the Ligand 3-nickel complex with the Ligand 4-nickel complex. See FIG. 8 and Table 1 for analytical results data.

Comparative Example C

Figure 9:
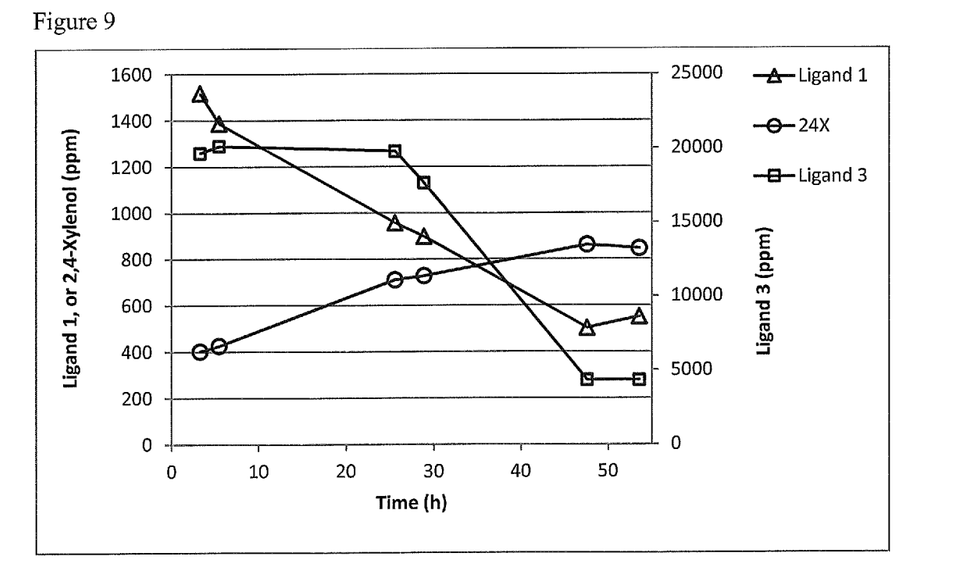
FIG. 9 is a graph showing the time course of hydrolysis of a mixture of Ligand 3, and Ligand 1 in valeronitrile, wherein the nickel phosphite complex formed from Ligand 3 is present in the mixture.

Hydrolysis of a Mixture of Ligand 1 and Ligand 3 in Valeronitrile, Wherein the Nickel Phosphite Complex Formed from Ligand 3 is Present in the Mixture Example 1 was replicated, but use valeronitrile instead of pentenenitrile as the solvent. See FIG. 9 and Table 1 for analytical results data.

Example 2

Synthesis of Phosphonates from Ligand 2, Using the Nickel Complex Formed from Ligand 3

A solution of 1.2% Ligand 2 in PNs was substantially hydrolyzed with 2500 ppm water, and 500 ppm ZnCl2, at 75°

C., overnight. Analysis of the reaction mixture by HPLC showed quantitative conversion of the Ligand 2, and GCMS analysis indicated that primarily the first hydrolysis product was formed. To the reaction mixture was then charged an aliquot of the Ligand 3-Ni complex so that the concentration of nickel in solution was approximately 1%, and then heating was continued for 5 days. After this time, the solution was analyzed by GCMS and $^{31}$P-NMR, which revealed the formation of a complex mixture of the butenyl- and cyanobutyl-phosphonate derivatives. No remaining hydrolysis products were present. See Table 1 for analytical results data.

Comparative Example D

Attempted Synthesis of Phosphonates from Ligand 2, Using Ligand 5-Nickel Complex Example 2 was replicated, but using the nickel complex of Ligand 5. Only the hydrolysis product of Ligand 2 was found. No phosphonate formation was observed. See Table 1 for analytical results data.

Example 3

Synthesis of Phosphonates from Ligand 1, Using the Nickel Complex Formed from Ligand 3

Example 2 was replicated, but replacing Ligand 2 with Ligand 1. See Table 1 for analytical results data.

TABLE 1

Summary of Results for Examples 1-3 and Comparative Examples

| Ex/CEx | Ligand | Free phosphites present | % Ligand consumed | solvent | Butenyl-phosphonates formed | Cyanobutyl-phosphonates formed |
|---|---|---|---|---|---|---|
| 1 | 3 | 1, 2, 3 | 0 | PN | Yes | Yes |
| A | — | 1, 2, 3 | 89 | PN | No | No |
| B | 4 | 4, 2 | 44 | PN | Yes | No |
| C | 3 | 3, 1 | 81 | VN | No | No |
| 2 | 3 | 2 | 0 | PN | Yes | Yes |
| D | 5 | 2 | 31 | PN | No | No |
| 3 | 3 | 1 | 0 | PN | Yes | Yes |

In Table 1, the following abbreviations are used. PN: mixed pentenenitriles (~87% 3PN), VN: valeronitrile, Ligand: phosphite coordinated to nickel The data presented in Table 1 show that the Ligand 3 nickel complex catalyzes the formation of phosphonates from the hydrolysis products of phosphites, as shown by Examples 2, and 3, and is more effective than Ligand 5, as evidenced by Comparative Example D. Additionally, the Ligand 3 Ni complex protects the phosphites of reaction mixtures resulting from the catalytic hydrocyanation of PNs to adiponitrile by against autocatalytic hydrolysis, as shown by comparison of Example 1 to Comparative Example A. Further, the Ligand 3 Ni complex is demonstrated to be advantaged over other diphosphite-nickel complexes, as shown by comparison of the data from Example 1 and Comparative Example B. Additionally, it was demonstrated that in a non-olefinic solvent system, such as valeronitrile, in which phosphonate formation is not possible, that autocatalytic phosphite hydrolysis does proceed, further illustrating phosphonate formation as a mode of protection against autocatalytic phosphite hydrolysis, as shown by comparison of the data of Example 1 and Comparative Example C.

Although not shown here, control experiments conducted under the same conditions to those in Table 1, but with no water present, showed no phosphite consumption, or phosphonate formation.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred features and optional features, modification and variation of the concepts herein disclosed may be resorted to by those skilled in the art, and that such modifications and variations are considered to be within the scope of this invention as defined by the appended claims.

What is claimed is:

1. A method of forming a phosphonate diester compound of formula (I)

wherein
each Ar is independently an unsubstituted or a mono-substituted or a multi-substituted aryl group, wherein any aryl group can be substituted with independently selected (C1-C4)alkyl, hydroxyl, a phosphite ester group, or phosphonate ester group; or,
the two Ar groups are bonded to each other to provide an unsubstituted or substituted biaryl derivative, wherein the biaryl derivative is unsubstituted or is independently mono-substituted or multi-substituted with independently selected (C1-C4)alkyl, hydroxyl, a phosphite ester group, or a phosphonate ester group; and, R is a 2-butenyl, 3-butenyl, 2-cyanobutyl, 3-cyanobutyl, or 4-cyanobutyl group;

the method comprising contacting in a reaction zone a diaryl phosphite compound of formula (III), (III)

wherein Ar is as defined for the compound of formula (I), a pentenenitrile, hydrogen cyanide, a Lewis acid, and water, in the presence of a nickel catalyst comprising a bidentate phosphite ligand of formula (IV)

(IV)

wherein $R^1$ and $R^2$ are each independently an unsubstituted or a substituted monovalent aryl, and each of $R^3$-$R^{10}$ is independently selected from the group consisting of hydrogen, (C1-C10) alkyl, and (C1-C10)alkoxy, or wherein two adjacent $R^3$-$R^{10}$ groups together form an optionally substituted fused aryl ring, under conditions suitable for hydrocyanation of the pentenenitrile to occur.

2. The method of claim 1 wherein for the bidentate phosphite ligand of formula (IV), $R^1$ and $R^2$ are both mono-ortho-substituted aryls, wherein the $R^1$ and $R^2$ aryl groups are each ortho-substituted with one respective (C1-C10)alkyl or (C1-C10)alkoxy group, provided that respective meta- and para-positions of the $R^1$ and $R^2$ aryls can be unsubstituted or substituted.

3. The method of claim 1 wherein for the bidentate phosphite ligand of formula (IV), $R^6$ and $R^{10}$ are not hydrogen.

4. The method of claim 1, wherein for the bidentate phosphite ligand of formula (IV), at least one of $R^3$, $R^4$, and $R^5$, and at least one of $R^7$, $R^8$, and $R^9$, is not hydrogen.

5. The method of claim 1, wherein for the bidentate phosphite ligand of formula (IV), $R^5$ and $R^6$ together form an optionally (C1-C10)alkyl-substituted or a (C1-C10)alkoxy-substituted fused phenyl ring, and wherein $R^9$ and $R^{10}$ together form an optionally (C1-C10)alkyl-substituted or a (C1-C10)alkoxy-substituted fused phenyl ring.

6. The method of claim 1, wherein for the bidentate phosphite ligand of formula (IV), $R^1$ and $R^2$ are both mono-ortho-substituted aryls and the aryls are ortho-substituted with a (C1-C10)alkyl or a (C1-C10)alkoxy, $R^6$ and $R^{10}$ are a (C1-C10)alkyl or a (C1-C10)alkoxy, and at least one of $R^3$-$R^5$, and at least one of $R^7$-$R^9$, is a (C1-C10)alkyl or a (C1-C10)alkoxy.

7. The method of claim 1 wherein the pentenenitrile is 3-pentenenitrile.

8. The method of claim 1 wherein $R^1$ and $R^2$ are 2,4-xylyl.

9. The method of claim 1 wherein $R^3$ and $R^7$ are isopropyl, $R^4$ and $R^8$ are hydrogen, or $R^5$, $R^6$, $R^9$ and $R^{10}$ are methyl, or any combination thereof.

10. The method of claim 1 wherein the bidentate phosphite ligand of formula (IV) is (Ligand 3)

or is (Ligand 4)

* * * * *